US 6,627,878 B1

(12) United States Patent
Machlinski et al.

(10) Patent No.: US 6,627,878 B1
(45) Date of Patent: *Sep. 30, 2003

(54) (CHEMICAL AGENT) POINT DETECTION SYSTEM (IPDS) EMPLOYING DUAL ION MOBILITY SPECTROMETERS

(75) Inventors: Kevin J. Machlinski, Crofton, MD (US); Michael A. Pompeii, Fredericksburg, VA (US); Gregory P. Johnson, Fredericksburg, VA (US); Robert A. Fitzgerald, Fredericksburg, VA (US); Jonathan A. Byrne, King George, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 19 days.

This patent is subject to a terminal disclaimer.

(21) Appl. No.: 09/853,926

(22) Filed: May 9, 2001

Related U.S. Application Data

(63) Continuation-in-part of application No. 09/613,995, filed on Jul. 11, 2000, now Pat. No. 6,459,079.
(60) Provisional application No. 60/266,098, filed on Feb. 1, 2001.

(51) Int. Cl.[7] .......................... B01D 59/44; G01T 1/18; H01J 49/40
(52) U.S. Cl. ...................... 250/287; 250/286; 250/288; 250/382
(58) Field of Search .................. 250/286, 287, 250/382, 282, 288; 73/863.12, 1.06

(56) References Cited

U.S. PATENT DOCUMENTS

| 3,307,033 | A | * | 2/1967 | Vestal ........................ 250/290 |
| 3,666,382 | A | | 5/1972 | Rasmussen et al. ........ 250/41.9 |
| 3,699,333 | A | * | 10/1972 | Cohen et al. ................ 250/282 |
| 4,136,280 | A | * | 1/1979 | Hunt et al. .................. 250/292 |
| 4,311,669 | A | * | 1/1982 | Spangler ....................... 422/98 |
| 4,445,038 | A | | 4/1984 | Spangler et al. ............. 250/382 |
| 4,551,624 | A | * | 11/1985 | Spangler et al. ............. 250/287 |
| 4,732,046 | A | * | 3/1988 | Lawrence et al. ........ 73/864.21 |
| 4,820,920 | A | | 4/1989 | Bather ......................... 250/282 |
| 4,839,143 | A | * | 6/1989 | Vora et al. ..................... 422/98 |
| 4,855,595 | A | * | 8/1989 | Blanchard .................... 250/287 |
| 4,988,628 | A | | 1/1991 | Nanji .......................... 436/173 |
| 5,083,019 | A | | 1/1992 | Spangler ...................... 250/286 |
| 5,095,206 | A | * | 3/1992 | Bacon, Jr. et al. .......... 250/282 |
| 5,109,157 | A | * | 4/1992 | Loen ........................... 250/287 |
| 5,162,649 | A | | 11/1992 | Burke .......................... 250/288 |
| 5,162,652 | A | * | 11/1992 | Cohen et al. ................ 250/288 |
| 5,200,614 | A | * | 4/1993 | Jenkins ........................ 250/286 |
| 5,227,628 | A | | 7/1993 | Turner ......................... 250/281 |
| 5,300,773 | A | | 4/1994 | Davies ......................... 250/286 |
| 5,310,681 | A | * | 5/1994 | Rounbehler et al. ........ 436/106 |
| 5,313,061 | A | | 5/1994 | Drew et al. .................. 250/281 |
| 5,338,931 | A | * | 8/1994 | Spangler et al. ............. 250/287 |
| 5,345,809 | A | | 9/1994 | Corrigan et al. ............. 73/23.2 |
| 5,371,364 | A | * | 12/1994 | Davies et al. ................ 250/287 |
| 5,405,781 | A | * | 4/1995 | Davies et al. .................. 436/52 |
| 5,420,424 | A | * | 5/1995 | Carnahan et al. ........... 250/287 |
| 5,455,417 | A | | 10/1995 | Sacristan ..................... 250/287 |

(List continued on next page.)

Primary Examiner—Andrew H. Hirshfeld
Assistant Examiner—Wasseem H. Hamdan
(74) Attorney, Agent, or Firm—Matthew J. Bussan, Esq.; James B. Bechtel, Esq.; Raymond H. J. Powell, Jr., Esq.

(57) ABSTRACT

A system for sampling the ambient air of a selected environment for the presence of unwanted chemical vapors, such as nerve or blister gases includes an external air sampling unit and a detector unit having first and second ion mobility spectrometers which simultaneously detect and monitor for the presence of the chemical agent vapors so as to provide an accurate and quick determination of the unwanted chemical vapor within the selected environment.

16 Claims, 4 Drawing Sheets

U.S. PATENT DOCUMENTS

| | | | |
|---|---|---|---|
| 5,457,316 A | | 10/1995 | Cohen et al. ................ 250/286 |
| 5,465,480 A | * | 11/1995 | Karl et al. ..................... 29/825 |
| 5,491,337 A | | 2/1996 | Jenkins et al. .............. 250/287 |
| 5,587,581 A | | 12/1996 | Stroosnyder ................ 250/287 |
| 5,723,861 A | * | 3/1998 | Carnahan et al. ........... 250/287 |
| 5,736,739 A | | 4/1998 | Uber et al. ................. 250/287 |
| 5,801,379 A | * | 9/1998 | Kouznetsov ................ 250/282 |
| 5,834,771 A | * | 11/1998 | Yoon et al. ................. 250/286 |
| 5,859,362 A | * | 1/1999 | Neudorfl et al. ............. 73/23.2 |
| 5,952,652 A | | 9/1999 | Taylor et al. ................ 250/286 |
| 5,965,882 A | | 10/1999 | Megerle et al. .............. 250/287 |
| 6,064,070 A | | 5/2000 | Schnurpfeil et al. ........ 250/423 |
| 6,085,601 A | * | 7/2000 | Linker et al. ............ 73/863.12 |
| 6,144,029 A | * | 11/2000 | Adler ......................... 250/288 |
| 6,225,623 B1 | * | 5/2001 | Turner et al. ................ 250/286 |
| 6,239,428 B1 | * | 5/2001 | Kunz ......................... 250/287 |
| 6,291,821 B1 | * | 9/2001 | Danylewych-May et al. .... 250/286 |

* cited by examiner

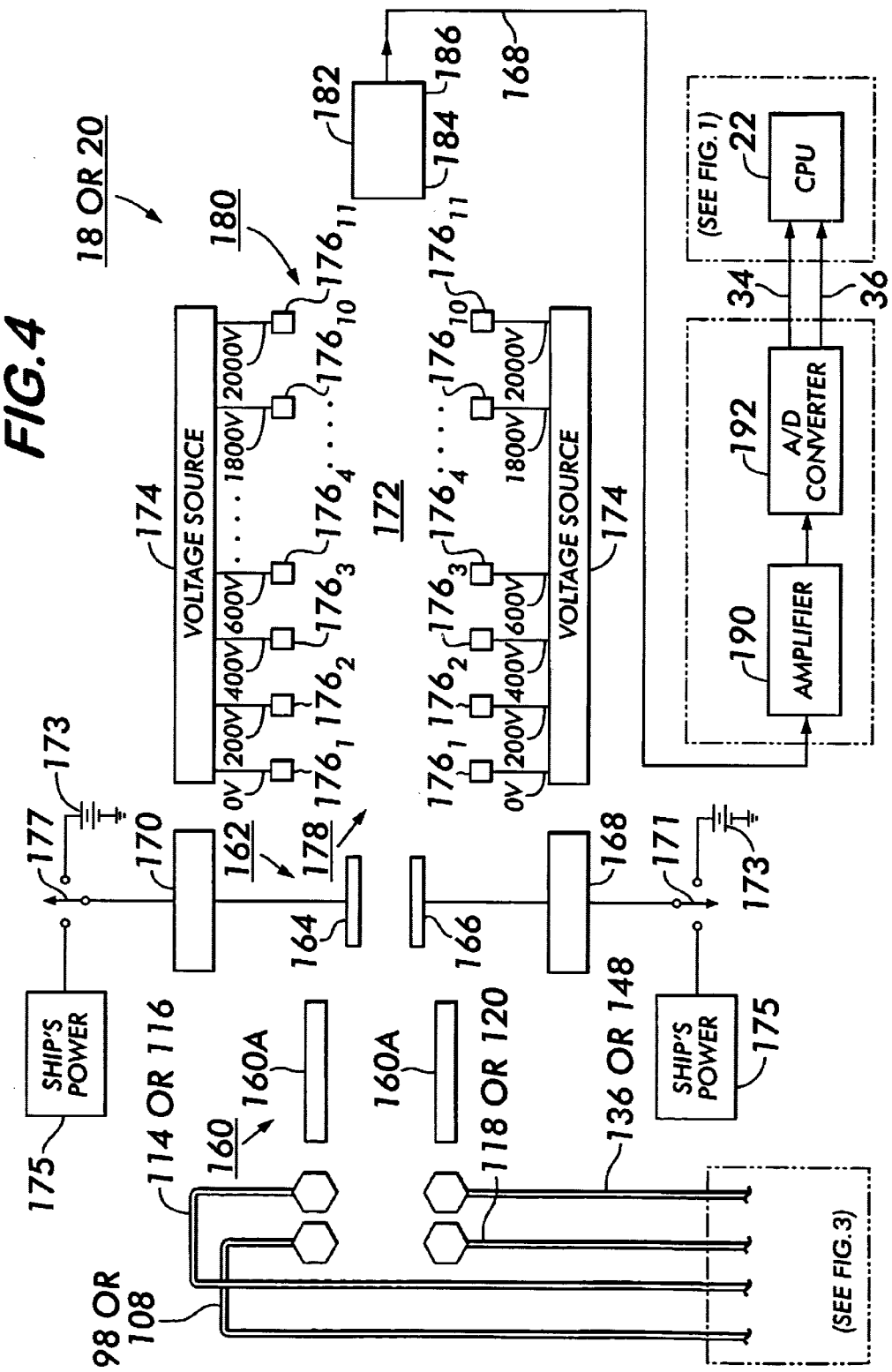

US 6,627,878 B1

(CHEMICAL AGENT) POINT DETECTION SYSTEM (IPDS) EMPLOYING DUAL ION MOBILITY SPECTROMETERS

CROSS-REFERENCE TO RELATED APPLICATIONS

This application is Continuation-in-Part of the invention described in U.S. patent application Ser. No. 09/613,995, which was filed on Jul. 11, 2000, and which issued as U.S. Pat. No. 6,459,079 B1 on Oct. 1, 2002. Moreover, this application claims priority from Provisional Patent Application No. 60/266,098, which was filed on Feb. 1, 2001.

STATEMENT OF GOVERNMENT INTEREST

The invention described herein may be manufactured and used by or for the Government of the United Statement of America for governmental purposes without the payment of any royalties thereon or therefor.

BACKGROUND OF THE INVENTION 1.0 Field of the Invention

The present invention relates to a system used to analyze compositions to determine what chemical elements are present therein and, more particularly, to a system that analyzes an air sample and, if undesired chemical vapors are present therein, provides signals to activate alarms.

2.0 Description of the Related Art

The ambient by which one is surrounded is of utmost importance. However, the ambient may suffer from pollution that allows the surrounding atmosphere to be contaminated, especially by man-made waste and vapor pollutants.

The environment by which one is surrounded may also be invaded by more serious pollutants, especially during terrorist situations or during warfare, in particular, biological warfare. Biological warfare involves the use of living organisms (as disease germs) or their toxic products, such as blister and nerve gases, that attack humans, animals, or plants, with the human suffering severe bodily pain.

Systems for measuring samples to determine the contents thereof are known and some of which may employ ion mobility spectrometers (IMSs), such as described in U.S. Pat. Nos. 4,445,038; 5,083,019; 5,300,773; 5,491,337 and 5,587,581, and all of which are herein incorporated by reference. The IMS provides a quantitative measurement of the contents of the molecules being sampled by measuring a time of "flight" of the ions of the molecules through a drift region of the IMS which is determined by the ion mobility characteristic of the ions being sampled and which, in turn, provides the identity and the concentration of the composition being measured. The IMS of the prior art serves well its intended purposes, but it is desired that further improvements to the IMS system be provided.

Accordingly, it is desired that means be provided employing ion mobility spectroscopy technology that analyzes the environment to detect the presence of unwanted chemical agent vapors found in pollutants and, more particularly, in biological warfare agents. More particularly, it is desired that an Ion Mobility Spectrometer (IMS) be provided that yields a quick and improved accurate determination of these unwanted chemical agent vapors so that the environment may be quickly purged thereof.

OBJECTS OF THE INVENTION

It is a primary object of the present invention to provide a system utilizing an IMS that accurately detects and monitors for the presence of undesired chemical agent vapors in an environment.

It is another object of the present invention to provide a system employing an IMS that quickly, yet accurately, detects and monitors for the presence of undesired chemical vapors in an environment and, upon detection thereof, provides an alarm indication.

Another object of the present invention is to provide a system having at least first and second configurations so that an alarm condition is only generated if there is an agreement between the detection derived separately from the first and second configurations.

In addition, it is an object of the present invention to provide a system employing first and second IMSs to advantageously detect ions having both predominate positive and negative polarities, respectively, so as to simultaneously detect separate gaseous samples having respective positive and negative charge characteristics.

It is another object of the present invention to provide for an instrument that uses ion mobility spectroscopy technology that analyzes molecules of chemical agent vapors by determining the cluster arrangement of the ions making up the chemical vapor agents and conditions the molecules of selected vapors so that these molecules are more easily and accurately detected by an IMS operated to more advantageously detect ions manifesting a positive charge.

Furthermore, it is an object of the present invention to provide for an ion mobility spectrometer (IMS) that generates an electrical signal which is routed to one of circuitry and software for comparing the electrical signal against predetermined signals indicative of unwanted and/or dangerous compositions of gaseous vapors, and if a match exists therebetween, an alarm is generated.

SUMMARY OF THE INVENTION

The invention is directed to a system for sampling the ambient of a selected environment for the presence of unwanted, predetermined chemical vapors therein.

The system includes a device for obtaining a sample of the selected environment and structure for conditioning the sample into a vapor containing known molecules. The system also includes a device for receiving the vapor made up of ion clusters that define ions of the molecules. The receiving device can include first and second ion mobility spectrometers with one of the ion mobility spectrometers having arranged therewith a reagent source. Each of the first and second ion mobility spectrometers provides an electrical signal representative of the respectively received defined ions of the molecules, if desired, the system also includes circuitry for comparing each of the representative electrical signals of the first and second ion mobility spectrometers against predetermined signals representative of predetermined chemical vapors and for generating an alarm signal if a match exists therebetween.

BRIEF DESCRIPTION OF THE DRAWINGS

A better understanding of the present invention may be realized when considered in view of the following detailed description, taken in conjunction with the accompanying drawings wherein:

FIG. 4 is a schematic of the IMS cells of FIG. 1.

DETAILED DESCRIPTION OF THE PREFERRED EMBODIMENTS

Figure 1:
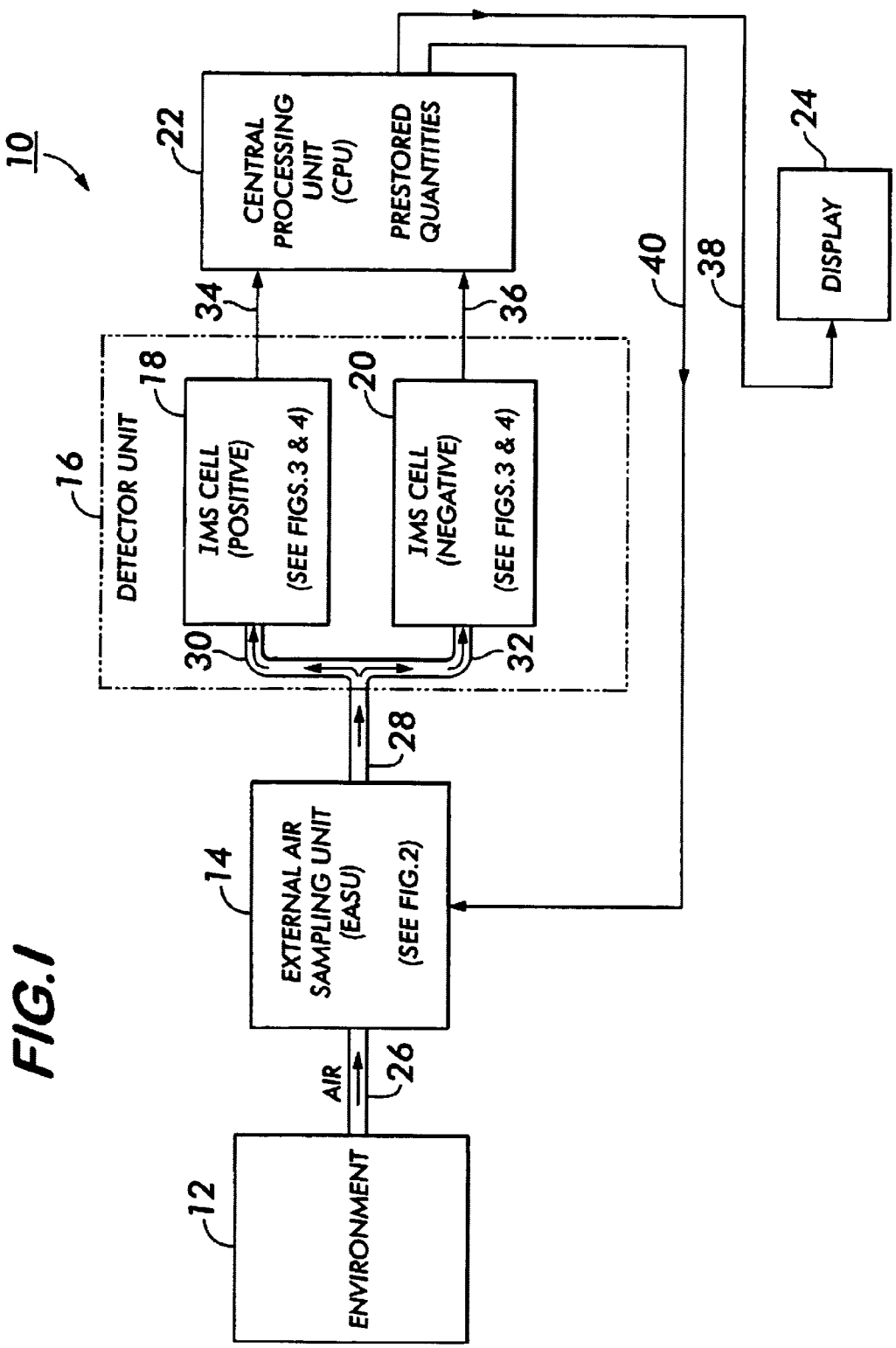
FIG. 1 is a block diagram of the system of the present invention.

Referring to the drawings, wherein the same reference number indicates the same element throughout, there is shown in FIG. 1 a block diagram of the system 10 of the present invention. The system 10 samples the ambient of a selected environment 12 by means of an external air sampling unit (EASU) 14, a detector unit 16 including an ion mobility spectrometer (IMS) cell (POSITIVE) 18 and an ion mobility spectrometer (IMS) cell (NEGATIVE) 20, a central processing unit (CPU) 22 having prestored quantities, and preferably a display 24. The EASU 14 serves as means for obtaining a sample of the selected environment 12 and as means for conditioning the sample into a treated vapor containing known molecules. The detector unit 16 serves as means for receiving and ionizing the treated vapors into cluster arrangements that define ions of the molecules and as means for receiving the clusters of the defined ions and providing corresponding electrical signals thereof. The CPU 22 serves as the means for comparing the electrical signals generated by the detector unit 16.

The system 10 employs at least one detector unit 16 having at least two ion mobility spectrometers 18 and 20, with the ion mobility spectrometer 18 operating in a mode to detect ions predominately having a positive polarity and operatively cooperating with a reagent source that treats an associated portion of sample being measured so as to be more easily detected by the ion mobility spectrometer 18 operating in the positive mode.

In general, the EASU 14 draws air, along flow path 26, which serves as a sample from the selected environment 12. The EASU 14 conditions the sample and delivers the sample on to flow path 28 which, in turn, is delivered to IMS cell 18 via flow path 30 and to IMS cell 20 via flow path 32. The IMS cells 18 and 20 provide electrical signals on signal paths 34 and 36, respectively, that are routed to a central processing unit 22. The central processing unit 22 compares the received signals on signal path 34 and 36 against prestored quantities and, if a comparison exists therebetween, provides an electrical signal on signal path 38 that is delivered to display 24 indicative of the alarm. The prestored quantities are electrical signals representative of gaseous vapors of unwanted or dangerous compositions, such as nerve or blister gases used in biological warfare, or pollutants that can contaminate the environment 12 being monitored. The CPU 22 also provides a control signal on signal path 40 that is routed to EASU 14.

FIG. 1 illustrates a system 10 referred to herein as a point detection system comprised of an arrangement of a single EASU 14 and a single detector unit 16 and allows the CPU 22 to generate an error signal upon the detection of an alarm condition therein. If desired, this system 10 may include a dual arrangement (not shown) having two separate EASUs 14 and two separate detector units 16, each of which is operatively interconnected so that the CPU 22 does not generate an error signal unless there is an agreement between the measurements of the quantities detected by the dual, yet separate, arrangements.

In general, each of the ion mobility spectrometer (IMS) cells 18 and 20 accepts ions in a vapor sample, and then separates those ions in an electric field. The acceleration of the ion in an electric field is a function of its charge and mass; at atmospheric pressure, the acceleration is a function of its shape and size as well. The characteristic that tells how fast a particular ion can move through an electric field at a given temperature and pressure is called the mobility of the ion, i.e., ion mobility, and, as such, is an indication for determining the make up of the molecules of the vapor sample being analyzed and measured by the IMS cells 18 and 20.

At atmospheric pressure, ions and molecules can cluster together in a way unique to the molecule producing the ions. This clustering does not need to be with similar molecules. These non-similar molecules are called reagents. As used herein, G-agent vapor molecules cluster with acetone molecules, forming positively charged cluster ions. As further used herein, H-agent vapor molecules cluster with hydroxyl ions to form negatively charged cluster ions. Furthermore, as used herein, a single-agent ion clustered with reagent molecules is called a monomer. Further still, as used herein, a two and a three-agent molecule clustered with reagent molecules is called a dimmer and a trimmer, respectively.

In the separation method of the IMS cells 18 and 20 to be further discussed with reference to FIG. 4, the ions start from rest at the same time and travel a known distance along a drift region having a high-voltage gradient which is applied thereto. A cathode electrode is located at the end of the drift region in each IMS cells 18 and 20 to detect the traveling ions. The smaller ion clusters have greater mobility and reach the end of the drift region first, as compared to other clusters. Heavier clusters arrive later at the cathode electrode and their arrival time is on the order of their mass. The ion mobility is sometimes referred to as determining the time of "flight," as more fully discussed in the previously incorporated by reference U.S. Pat. No. 5,587,581('581). As used herein, the arrival time at the cathode electrode is primarily a measure of the size and shape of the cluster ions.

Each substance or composition operated on by each of the IMS cells 18 and 20 that can be ionized produces a unique electrical IMS signal. As will be further described with reference to the CPU 22, an unknown substance can be identified by comparing its unique IMS signal, also called its IMS signature, with a set of previously recorded signatures of known substances making up a reference library. The waveforms of the IMS signature may have peaks that represent information regarding the identity and concentration of the samples being measured in a manner more fully described in the '581 patent. The reference library may be made up to identify any substance at any concentration thereof with such substances being, for example, nerve or blister gases. If the IMS signature of the unknown substance matches one of the known signatures in the reference library, that unknown substance is identified. The substances sampled by the present invention are conditioned by the EASU 14 which will be further described with reference to FIG. 2.

Figure 2:
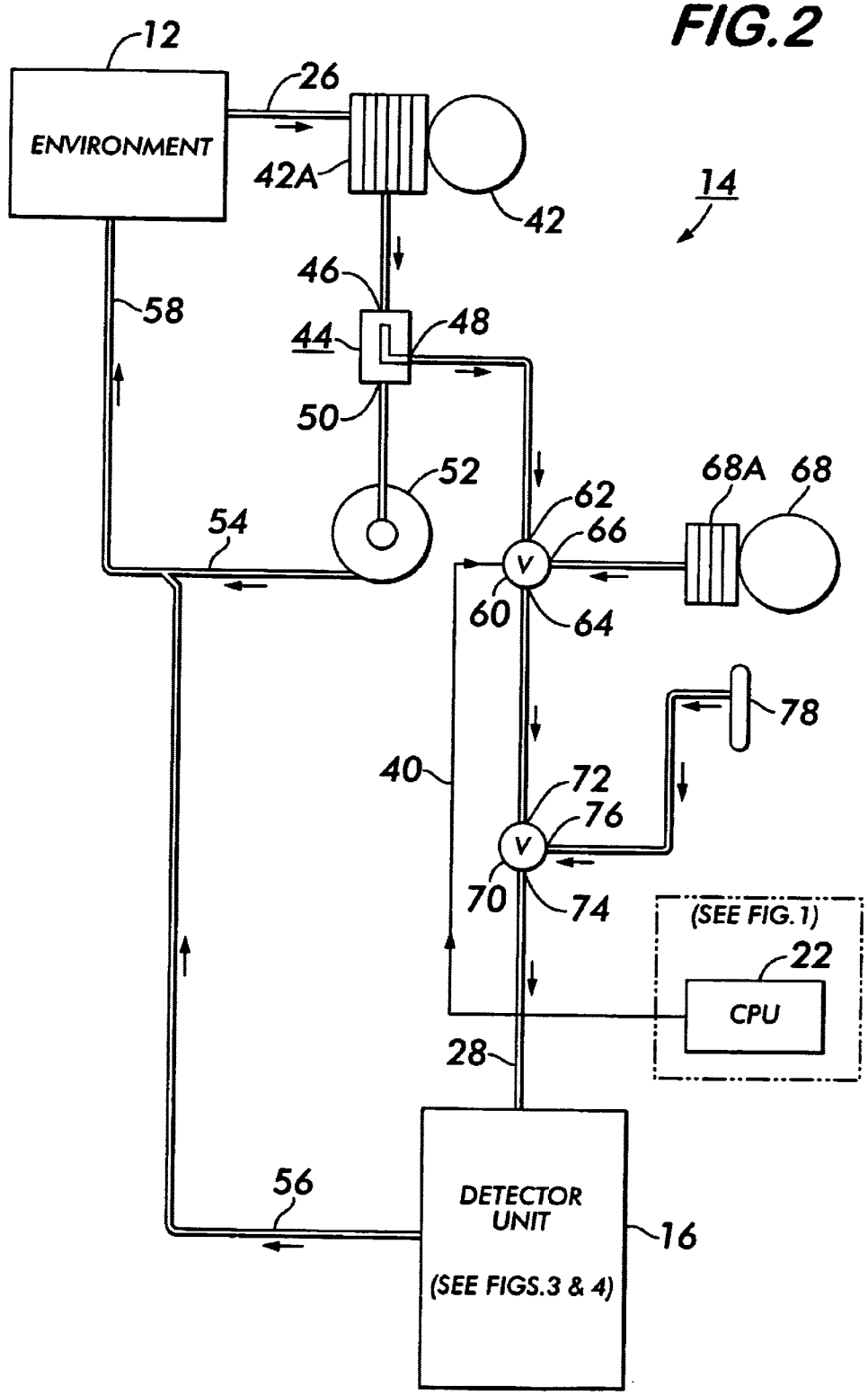
FIG. 2 is a schematic of the external air-sampling unit of FIG. 1.

As illustrated in FIG. 2, the EASU 14 gathers a relatively large amount of an ambient sample air surrounding or within the selected environment 12, which may be a ship or any compartment therein. The air is typically gathered by an inlet groove or opening that protrudes through the exterior bulkhead and into the ambient air surrounding the ship or the compartment. The air is pulled into the EASU 14 on flow path 26 and has a typical first flow rate of 30 CFM so as to ensure that an encompassing representative sample is taken for analysis and measurement thereof. The air may be drawn in by employing an air pump 42 having a particulate filter 42A arranged therewith. The air pump 42, as well as other sample and recirculating pumps of the present invention, may be a 24 volt D.C. centrifugal, graphite-vane pump, known in the art.

Once the sampled air enters the EASU 14, it passes through the particulate filter 42A and by a pitot tube 44, known in the art designed to collect a much smaller sample, relative to the 30 CFM first flow rate, for the detector unit 16, to be described, to analyze. The pitot tube 44 has first, second and third ports 46, 48 and 50, with the first port 46 receiving the sample at the first flow rate, that is 30 CFM, the second port 48 making available the sample at a second flow rate, and the third port 50 making available a fluid flowing at a flow rate which is the difference between the first and second flow rates. The Pitot tube 44 provides the sample at the second port 48 at the second flow rate which is less than the first flow rate, e.g., 4.5 LPM. The third port 50 has fluid communications with an exhaust pump 52 that presents the excessive external air (sample at first flow rate sample at second flow rate) to the environment on flow path 54, which is merged with fluid flow path 56 of the detector unit 16 both of which flows are directed into flow path 58 which, in turn, is directed back into the selected environment 12. The second port 48 of Pitot tube 44 is routed to valve 60, which may be an electric three (3)-way solenoid valve, responsive to an electric signal. The electrical signal delivered on path 40 may be generated by CPU 22 (previously described with reference to FIG. 1). The CPU 22 generates the electrical signal on path 40 to cause the valve 60 to allow the sample at the second flow rate to pass therethrough so that it may be measured and analyzed downstream by the detector unit 16.

Preferably, the valve 60 has at least first and second ports 62 and 64, but preferably a third port 66, with the first port 62 arranged to receive the sample flowing at the second flow rate and the second port making available the sample at the second flow rate at the output of the valve 60.

The third port 66 of the electric three (3)-way solenoid valve, serving as a purge port 66, is in fluid communications with a purge filter 68A that has an operative arrangement with a purge blower 68. The purge blower 68, in cooperation with the purge filter 68A, provides for the ability to purge the system 10. More particularly, the operation of the purge blower 68, in cooperation with the valve 60 being arranged so that the third and second ports 66 and 64 are in fluid communication with each other, causes the fluid communication paths from the valve 60 to and within the detector unit 16 to be purged of any unwanted vapor residue. The desired arrangement of valve 60 may be accomplished by appropriate usage of the electric signal on signal path 40 generated by the CPU 22. The second port 64 of the valve 60 is preferably in fluid communication with a valve 70, which may be a manual three (3)-way valve.

The three (3)-way manual valve 70 has at least first and second ports 72 and 74, but preferably also a third port 76, with the first port 72 being fluidly coupled to the second port 64 of the electric solenoid valve 60 and the second port 74 being fluidly coupled to the detector unit 16 via flow path 28. The flow path 28 is preferably established by one-quarter (¼) inch stainless steel tubing. The third port 76 of the three(3)-way manual valve 70 is in fluid communications with a sample 78, which may serve as a confidence sample that may be used in the calibration of the system 10. More particularly, the confidence sample 78 may be used to create IMS signatures on signal paths 34 and 36 of FIG. 1, which may be recognized by the application routines running in the CPU 22 so that a calibration check is generated, and which is indicative of the fact that the associated elements of the system 10 are operating correctly. The fluid communication path 28 may be further described with reference to FIG. 3, which is a schematic representation of the detector unit 16.

Figure 3:
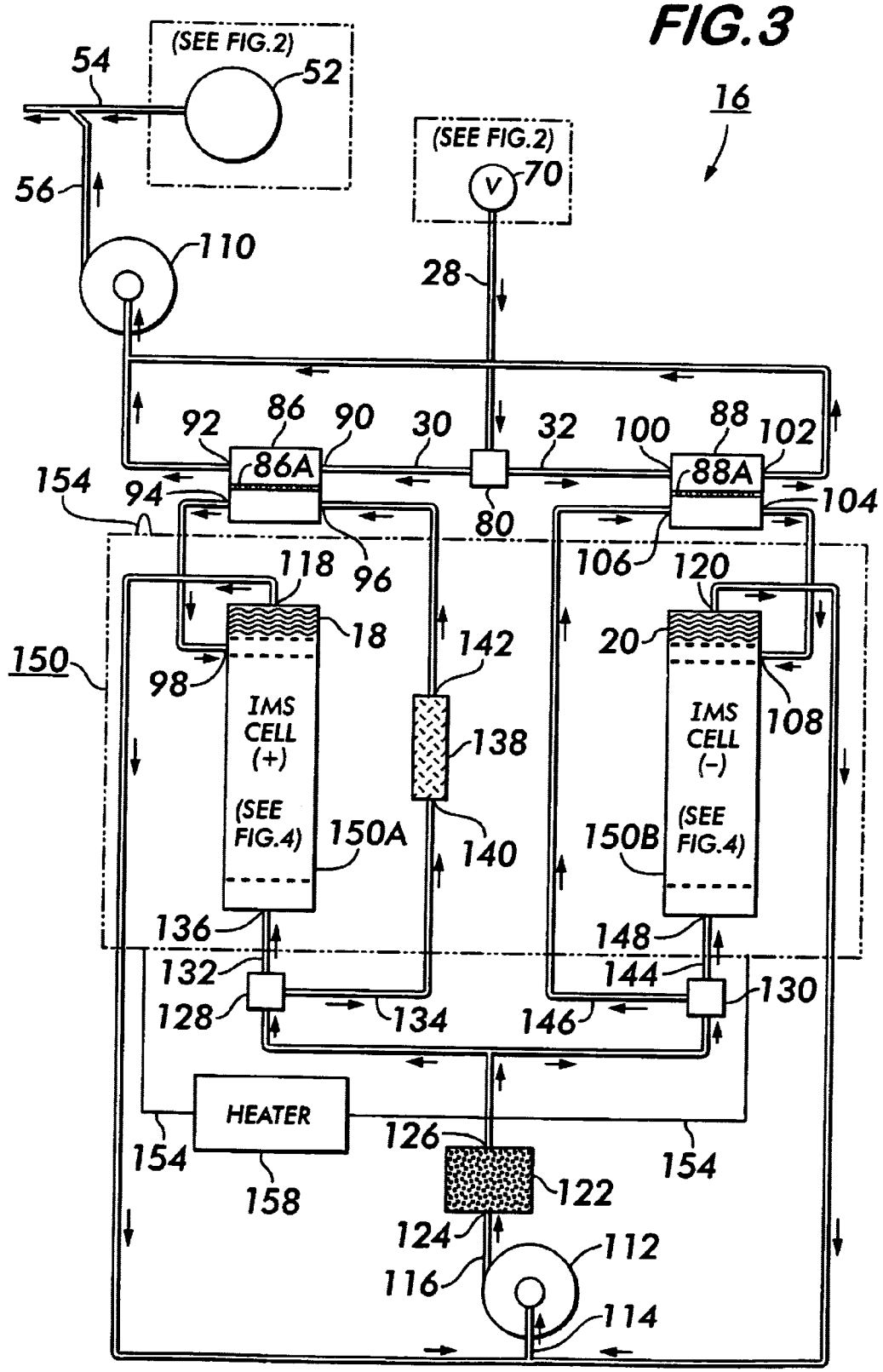
FIG. 3 is a schematic of the detector unit of FIG. 1.

As seen in FIG. 3, the fluid flow on path 28 having a second flow rate of 4.5 LPM, first encounters a valve 80 that serves as a dividing element that receives the sample at the second flow rate and separates the sample flowing at the second flow rate into fluid flow paths 30 and 32, respectively, (also shown in FIG. 1) having third and fourth flow rates which are substantially equal to one-half of the second flow rate. More particularly, the dividing element 80 divides the fluid flow on path 28 into two paths 30 and 32 each having a preferred flow rate of 2.25 LPM, which are respectively directed into canisters 86 and 88, each respectively containing semi-permeable membranes 86A and 88A.

The canister 86 has first, second, third and fourth ports 90, 92, 94, and 96, respectively, with the first port 90 having fluid communication with the fluid flow path 30 and the second port 92 accepting the fluid flow that does not migrate through the membrane 86A. The third port 94 is fluidly coupled to a port 98 of the IMS cell 18. The second canister 88 has first, second, third and fourth ports 100, 102, 104, and 106, respectively, which are fluidly coupled in a manner similar to those of canister 86. The port 104 of canister 88 is fluidly connected to port 108 of the IMS cell 20.

Each of the canisters 86 and 88 is preferably constructed of stainless steel and has a mount that holds a 1.0 mil-thick semi-permeable membrane 86A or 88A of a dimethyl silicone/polycarbonate hybrid material. The semi-permeable membranes 86A and 88A serve as selectors that selectively allow sample molecules of interest, such as those contained in nerve or blister gases or other pollutants contained in the sample being measured, into the IMS cells 18 and 20 while excluding excess water therefrom . As the air sample passes over each of the semi-permeable membranes 86A and 88A, a few sample air molecules migrate through the semi-permeable membranes 86A and 88A and get entrained in the recirculating air flows (to be described) of the detector unit 16. The few sample air molecules that pass through the semi-permeable membranes 86A and 88A are the only part of the original ambient air sample (first flow rate of 30 CFM) that actually gets analyzed by the IMS cells 18 and 20. If desired, the canisters 86 and 88 may be combined into one unit so long as all of the ports of the canisters 86 and 88 are provided therein.

The port 92 of canister 86 and the port 102 of canister 88 are fluidly coupled to the input of an air pump 110, which provides an output on fluid path 56, previously discussed with reference to FIG. 2.

The detector unit 16 further includes a recirculation path employing a first air pump 112 having an input 114 and an output 116. The input 114 is fluidly coupled to an air recirculation port 118 of the IMS cell 18 and also to an air recirculation port 120 of the IMS cell 20. The output 116 of the air pump 112 is fluidly connected to a cartridge 122 having an input 124 and an output 126 and containing a desiccant.

The desiccant cartridge 122 is interposed in the recirculating air of the detector unit 16 so as to clean and dry the recirculating air to ensure that the incoming sample of vapor, on flow path 28, is not contaminated by any interferants within the detector unit 16. The recirculating air of the detector unit 16 includes desiccant cartridge 122 that filters out all of the contaminates from the reduced air, that is, the sample air of the third and fourth flow rates on paths 30 and 32 respectively. The desiccant cartridge 122 may be filled with a molecular sieve material (size 4A) and a charcoal (untreated 6×16 mesh wire), which may be a BPL type known in the art. The molecular sieve material removes residual water vapor and the BPL charcoal removes any organic contaminants.

During operation, the desiccant cartridge 122 may typically become slowly loaded with contaminants and become unable, over a period of time, to maintain a clean and dry environment inside the recirculating air circuit of the detector unit 16 and, thus, desiring replacement thereof. The average life of the desiccant cartridge 122 is approximately 250 operating hours.

The output 126 of the desiccant cartridge 122 is routed to a second dividing element 128 and a third dividing element 130. The second and third dividing elements 128 and 130 may be valves similar to the first dividing element 80. The second dividing element 128 separates the fluid flowing at the fifth flow rate, that is, 2.25 LPM, into fluid flow paths 132 and 134 having sixth and seventh flow rates, wherein the sixth flow rate is greater than that of the seventh flow rate. More particularly, it is preferred that the sixth flow rate be approximately 1.8 LPM, whereas the seventh flow rate is preferred to be approximately 0.4 LPM. The sample flowing at the sixth flow rate is routed, via flow path 132, to port 136 of the IMS 18, whereas the seventh flow rate is routed, via flow path 134, to a reagent source 138 having an input port 140 and an output port 142.

The reagent source 138 may be an acetone vapor source consisting of a Teflon diffusion tube immersed in 50 mL of liquid acetone contained in a stainless steel vessel that is mounted next to the positive IMS cell 18. The output 142 of the reagent source 138 is routed to the port 96 of the canister 86. In operation, just prior to entering the positive IMS cell 18, the recirculating air within the detector unit 16 passes through the immersed tube of the reagent source 138 and the acetone molecules therein diffuse into the tube and mix with the recirculating air at a constant rate of approximately 675 mL/min at 180° F. The acetone molecules increase the positive polarity of the ions of the molecules being measured by the IMS cell 18 and, thus, increase the sensitivity of the positive IMS cell 18 operated in a manner to be further described with reference to FIG. 4.

A separate reagent vapor source similar to vapor source 138 is not required for the negative IMS cell 20. A small amount of residual atmospheric water vapor migrates through the semi-permeable membrane 88A of canister 88 with the sample vapor and enters the ionization chamber of the IMS cell 20, to be described. These water molecules act as the reagent for the negative polarity ion reactions within the IMS cell 20 and, thus, negate the need for a separate reagent vapor source for IMS cell 20.

The third dividing element 130 has a fluid flow paths 144 and 146, respectively carrying the sample at eighth and ninth flow rates, with the flow rate on paths 144 and 146 being that of paths 132 and 134, respectively. The sample at the eighth flow rate is routed via flow path 144 to a port 148 of the IMS cell 20, whereas the sample at the ninth flow rate is routed via flow path 146 to a port 106 of the canister 88.

Preferably, the components employed in constructing the IMS cells 18 and 20 are placed into a single canister 150. The container 150 has a heating element 154 operatively connected thereto. The heating element 154 advantageously can be constructed from a heater 158. The heater 158 is operated so as to preferably maintain the temperature of the IMS cells 18 and 20 at a constant temperature of about 180° F. The heating element 158 advantageously may be a 100 watt strip heater mounted under each of the cells 18 and 20 so as to maintain their temperature and to heat their surrounding components in order to prevent sample vapor condensing as it travels through the detector unit 16.

The IMS cells 18 and 20 may be further described with reference to FIG. 4 which is a schematic that is generically applicable to both the IMS cells 18 and 20, even though the IMS cell 18 predominately operates with positive potentials and the IMS cell 120 predominantly operates with negative potentials. The descriptions of the IMS cells 18 and 20 with reference to FIG. 4 are generic, but point out, as needed, the differences in the operation of the IMS cells 18 and 20.

FIG. 4 illustrates an ionization chamber 160, which, for the IMS cell 18, is referred to as the first ionization chamber and, for the IMS cell 20, is referred to as the second ionization chamber. The usage of this first and second terminology to refer to the IMS cells 18 and 20 respectively is used hereinafter throughout.

The first ionization chamber includes ports 98, 114, 118, and 136, whereas the second ionization chamber includes ports 108, 116, 120, and 140, all of which were previously described with reference to FIG. 3. Each of the first and second ionization chambers further include a radioactive source 160A. The radioactive source 160A is preferably of a 100 Ci of americium-241 ($Am^{241}$), which gives off beta particles that collide with the mixture of the sample-reagent molecules. The sample-reagent molecules of IMS cell 18 are those which have been treated by reagent source 138, whereas, as previously discussed, the sample-reagent molecules of IMS cell 20 do not need to be treated with a reagent source, such as reagent source 138. The reagent molecules ionize and react with the sample molecules to create ion clusters in a manner to be further described.

Each of the IMS cells 18 and 20 further comprises a gate 162, which is essentially consists of two wire grids 164 and 166 that are held at different voltage potentials. The gate 162 is held closed by means of a voltage potential difference applied across grids 164 and 166, with a positive (2000 V) potential being used for the positive IMS cell 18 and a negative (2000 V) potential being used for the negative IMS cell 20, with both positive and negative potentials being referenced to ground. More particularly, the grid 166 is at ground potential. The potential applied to the grid 166 is developed by a voltage source 168, whereas the potential applied to the grid 164 is developed by a voltage source 170. The voltage source 170 at predetermined intervals, such as 20 milliseconds, causes the voltage applied to the gate 162 (positive voltage in the positive IMS cell 18 and a negative voltage in the negative IMS cell 20) to be momentarily removed so that the potential difference between the grids 164 and 166 no longer exists which, in turn, causes the gate 162 to be opened allowing a small discrete amount of ion clusters of the molecules within the ionization chamber 160 to enter the drift region 172.

Each of the IMS cells 18 and 20 includes a drift region 172 whose operation is defined by a power supply 174, which supplies a potential to a plurality, e.g., 11, of circular electrodes $176_1$, $176_2$, $176_3$, $176_4$, ... $176_{10}$ and $176_{11}$, that are equally spaced apart from each other by insulated spacers (not shown). The electrodes $176_1$, ... $176_N$ are connected to the voltage source 174 so as to be sequentially and evenly increased by a voltage along the drift region so as to provide a predetermined voltage difference between an entrance portion 178 and an exit portion 180 of the drift region 172. For one embodiment, a potential difference from 0 to 2,000 volts is applied across the drift region in approximately 200 volt increments, creating a uniform electric field which accelerates ion clusters released into the drift region 172, by the operation of the gate 162, toward a collector or cathode electrode 182 that is electromagnetically coupled to the drift region 172.

The collector 182 has an input 184 and an output 186. The collector 182 provides an electrical output signal on signal path 188 which is preferably routed to a serial arrangement of an amplifier 190 and an analog-to-digital converter 192 so as to provide an electrical signal which, for the arrangement shown in FIG. 4, is a digital signal which in actuality is two digital signals (one for IMS 18 and another for IMS 20) that are respectively applied on signal paths 34 and 36 routed to the CPU 22.

Operation of the System of the Invention

In operation and with first reference to FIG. 3, the detector unit 16 receives the sample air flow at a second rate of 4.5 LPM, which is then split between the positive and the negative IMS cells 18 and 20, via the flow paths 30 and 32, respectively. The sample second flow rate is directed into the canisters 86 and 88 and directed across semipermeable membranes 86A and 88A. A few of the molecules of the sample migrate through the membranes 86A and 88A and are entrained in the circulating air flow of the detector unit 16. The remaining sample air is immediately exhausted out of the system via ports 92 and 102 of canisters 86 and 88, respectively.

The detector unit 16 has a recirculating air path formed essentially by air pump 112 and the dividers 128 and 130. The air pump 112 provides a recirculating air flow of 2.2 LPM, which is provided so as to maintain a clean and dry condition inside each of the IMS cells 18 and 20, all of the recirculating air is routed through the desiccant cartridge 122 containing a 40% molecular sieve material and an 80% activated BPL charcoal to remove any contaminants from the recirculating air flow.

The acetone vapor reagent source 138 is included in the recirculating airflow circuit of the positive IMS cell 18. This vapor reagent source 138 provides a trace amount the reagent molecules required for the reaction with the A-agent vapor molecules to form the positive ions predominant in the operation of the positive IMS cell 18. The negative IMS cell does not need a separate vapor reagent source because there is enough residual water is molecules in the air to form a hydroxyl ions (negative ions) needed to react with the H-agent molecules predominant in the operation of the negative IMS cell 20.

The two IMS cells 18 and 20 are provided, which is of importance to the present invention, so that IMS cells 18 and 20 operate simultaneously, one in the positive mode and the other in the negative mode. This capablity allows the system 10 to continuously detect both nerve (IMS cell 18) and blister (IMS cell 20) agent vapors.

The sample molecules that migrate through the semipermeable membranes 86A and 88A become entrained in the recirculating air that contains the reagent vapor molecules. This sample-reagent vapor mixture enters the ionization chamber 160 shown in FIG. 4 for both IMS cells 18 and 20. The ionization chamber 160 for each of the IMS cells 18 and 20 is surrounded by the radioactive source 160A which gives off beta particles that collide with the associated mixture of the sample-reagent molecules. The reagent molecules ionize and react with the sample molecules to create ion clusters for the molecules thereof.

The gate 162 of each of the IMS cells 18 and 20 is arranged so as to set up an electric field that prevents the ion clusters within the ionization region 160 from passing through into the drift region 172. However, at 20-milliseconds intervals, the voltage potential is removed from the gate 162 which correspondingly and momentarily removes the potential difference between the grids 164 and 166 making up gate 162. This "opens" the gate 162 and a small, discrete group of ions clusters enter the drift region 172.

As the ion clusters travel through the length of the drift region 172, the ion clusters separate due to their different ion mobility in the electric field and arrive at the collector 182 at different times, i.e., the smaller ion clusters have greater mobility and reach the collector 182 ahead of their heavier counterparts. As the ion clusters impact on the collector 182 they discharge and create a small ion current. This ion current is made available at the output 186 of the collector 182 in the form of a signal, which is amplified by amplifier 190 and converted to a digital voltage by the A/D converter 192 located in each of the IMS cells 18 and 20. This digital voltage at the output of each A/D converter 192 serves as an IMS signature of the sample vapor being measured by each of the IMS cells 18 and 20. These IMS signatures are then analyzed by the application routines running in the CPU 22.

The CPU 22 may be a Motorola 6800 processor having routines that analyze digital signals. More particularly, the application programs running in the CPU 22 operate in conjunction with prestored quantities, each indicative of a signature of a vapor of interest, such as a vapor that may be created by either nerve or blister gases. The CPU 22 compares the IMS signatures present on signal paths 34 and 36 (IMS cells 18 and 20, respectively) with the prestored quantities, and if a match exists therebetween, generates an alarm signal via signal path 38, which notifies the operator of the undesired condition.

It should now be appreciated that the present invention provides for an improved point detection system that samples the ambient of an environment and detects and monitors for the presence of unwanted chemical agent vapors. The detector unit uses two different ion mobility spectrometers (IMSs) to analyze the air sample, and if unwanted chemical vapors are detected, provides appropriate signals to activate visual displays.

Furthermore, it should be appreciated that the system 10 may be arranged into a dual configuration with each configuration having a separate EASU 14 and a separate detector unit 16, both of which provide the electrical signals to the CPU 22 which, in turn, only provides an alarm if there is an agreement between the measurements of the dual configuration.

Although the invention has been described relative to the specific embodiments thereof, there are numerous variations and modifications that will become readily apparent to those skilled in the art in the light of the above teaching. It is, therefore, to be understood that within the scope of the appended claims, the invention may be practiced other than as specifically described.

What we claim is:

1. A system for sampling the ambient of a selected environment for the presence of predetermined chemical vapors therein, the system comprising:
   (a) means for obtaining a sample of the selected environment to thereby generate an obtained sample;
   (b) means for conditioning the obtained sample into a vapor containing known molecules;
   (c) means for receiving the vapor into clusters that define ions of the molecules, the means comprising first and second ion mobility spectrometers, with only one of the ion mobility spectrometers having arranged therewith a reagent source, each of the first and second ion mobility spectrometers providing electrical signals representative of the respective received defined ions of the molecules; and
   (d) means for comparing each of the representative electrical signals of the first and second ion mobility spectrometers against predetermined signals representative of the predetermined chemical vapors and generating an alarm signal if a match exists between one of the representative electrical signals and one of the predetermined signals.

2. The system according to claim 1, wherein the means for obtaining the sample comprises:
   (a) means for drawing the sample from the environment at a first flow rate;
   (b) means for receiving the sample at the first flow rate and providing a second flow rate thereof which is less than the first flow rate; and
   (c) means responsive to a first electrical signal and having at least a first and second ports with the first port arranged to receive the sample at the second flow rate and the second port making available the sample at the second flow rate in response to the first electrical signal.

3. The system according to claim 1, wherein:
   the means for obtaining the sample outputs the obtained sample at a second flow rate responsive to a sample input at a first flow rate; and
   the means for conditioning the sample comprises:
   (a) first dividing means for receiving the sample at the second flow rate and separating the sample at the second flow rate into first and second paths respectively having third and fourth flow rates each of which is substantially equal to one-half of the second flow rate of the sample;
   (b) first and second permeable membranes each arranged in a respective canister which intercepts the sample and has first, second, third and fourth ports with the first port of each canister having fluid communication with the second path of the first dividing means and the second port of each canister accepting the flow of the sample that does not pass through the permeable membranes, the third and fourth ports being output and input ports respectively with the third port making available the flow of the sample that does pass through the permeable membranes, and
   (c) recirculating means comprising:
      (i) a first air pump having an input and an output and developing a fifth flow rate at its output which is less than either of the third and fourth flow rates;
      (ii) a cartridge containing a desiccant and having an input and output with the input of the cartridge being connected to the output of the first air pump;
      (iii) a second dividing means having means for being connected to the output of the cartridge and separating the fifth flow rate of the sample into first and second paths respectively having sixth and seventh flow rates with the sixth flow rate being greater than the seventh flow rate;
      (iv) a container housing the reagent source of the one of the ion mobility spectrometers and having an input and an output with the input of the container being connected to the seventh flow rate and the output of the container being connected to the fourth port of the canister having arranged therein the first permeable membrane; and
      (v) a third dividing means having means for being connected to the output of the cartridge and separating the fifth flow rate of the sample into first and second paths respectively having eighth and ninth flow rates with the eighth flow rate being greater than the ninth flow rate and with the second path carrying the flow flowing at the ninth flow rate and being connected to the fourth port of the canister having arranged therein the second permeable membrane.

4. The system according to claim 3, further comprising a second air pump having an input and an output with the input being connected to each of the second ports of the canisters having arranged therein the first and second permeable membranes.

5. The system according to claim 1, wherein:
   the ionization chamber of the first ion mobility spectrometer includes a first radioactive source; and
   the ionization chamber of the second ion mobility spectrometer includes a second radioactive source.

6. The system according to claim 5, wherein the radioactive source of each of the first and second ion mobility spectrometers comprises 100 Ci of americium-241 ($Am^{241}$).

7. The system according to claim 5, wherein the receiving means further comprises:
   (a) a gate of the first ion mobility spectrometer having first and second electrodes and having means for being electromagnetically coupled to the output of the ionization chamber of the first ion mobility spectrometer, with the second electrode thereof being connected to a ground potential and the first electrode thereof being connected to a first voltage source that removes a positive voltage potential therefrom at first periodic intervals;
   (b) a gate of the second ion mobility spectrometer having first and second electrodes and having means for being electromagnetically coupled to the output of the ionization chamber of the second ion mobility spectrometer with the second electrode thereof being connected to a ground potential and the first electrode thereof being connected to a second voltage source that removes a negative voltage potential therefrom at second periodic intervals;
   (c) a drift region of the first ion mobility spectrometer with entrance and exit portions and having means for being electromagnetically coupled to the gate of the first ion mobility spectrometer, the drift region of the first ion mobility spectrometer being defined by a third voltage source having evenly spaced apart electrodes which are connected to a voltage that sequentially and evenly increases along the drift region of the first ion mobility spectrometer so as to provide a predetermined voltage potential between the entrance and exit portions of the drift region of the first ion mobility spectrometer;
   (d) a drift region of the second ion mobility spectrometer with entrance and exit portions and having means for being electromagnetically coupled to the gate of the second ion mobility spectrometer, the drift region of the second ion mobility spectrometer being defined by a fourth voltage source having evenly spaced apart electrodes which are connected to a voltage that sequentially and evenly increases along the drift region of the second ion mobility spectrometer so as to provide a predetermined voltage potential between the entrance and exit portions of the drift region of the second ion mobility spectrometer;
   (e) a collector of the first ion mobility spectrometer having an input and an output with the input having means for being electromagnetically coupled to the exit portion of the drift region of the first ion mobility spectrometer and the output providing a first electrical signal; and
   (f) a collector of the second ion mobility spectrometer having an input and an output with the input having means for being electromagnetically coupled to the exit portion of the drift region of the second ion mobility spectrometer and the output providing a second electrical signal.

8. The system according to claim 7, wherein the first and second periodic intervals are about 20 ms.

9. The system according to claim 7, wherein spaced apart electrodes of the drift regions of the first and second ion mobility spectrometers each comprises eleven (11) electrodes and wherein the voltage of both the third and fourth voltage sources are of the D.C. type and are sequentially and evenly increased by two hundred volts, with the first electrode being at zero (0) volts so that the predetermined voltage difference between the entrance and exit portions of both the first and second drift regions is two thousand (2,000) volts.

10. The system according to claim 9, further comprising a first serial arrangement of an amplifier and an analog-to-digital converter having means for the amplifier to be electrically coupled to the output of the collector of the first ion mobility spectrometer and with the analog-to-digital converter providing a first digital signal and further comprising a second serial arrangement of an amplifier and an analog-to-digital converter and having means for the amplifier to be electrically coupled to the output of the collector of the second ion mobility spectrometer and with analog-to-digital converter providing a second digital signal.

11. The system according to claim 1, further comprising:
a converter which generates first and second digital signals responsive to the electrical signal generated by the first and second ion mobility spectrometers,
wherein the means for comparing comprises;
(a) means for storing and accessing predetermined signals representative of the predetermined chemical vapors;
(b) means for receiving the first and second digital signals; and
(c) means for comparing the first and second digital signals against each of the predetermined signals and generating an alarm signal if a match exists between one of the first and second signals and one of the predetermined signals.

12. The system according to claim 1, wherein the means for receiving the clusters of the defined ions is enclosed in a housing.

13. The system according to claim 12, wherein a heating means is disposed in the housing.

14. The system according to claim 13, wherein the heating means maintains the temperature of the housing at about 180° F.

15. A system for sampling the ambient of a selected environment for the presence of a plurality-of predetermined chemical vapors therein, comprising:
a sample filter having an upstream side fluidly coupled to the selected environment;
first and second retainers supporting first and second permeable membranes, respectively;
a sample pump pneumatically coupled to the downstream side of the filter via the first and second retainers, the sample pump discharging to the selected environment;
a first ion mobility spectrometer (IMS) generating a first electrical signal;
a second IMS generating a second electrical signal;
a recirculation pump fluidly coupled to respective outlets of the first and second IMSs;
a recirculation filter disposed downstream of the recirculation pump;
a manifold disposed downstream of the recirculation filter, which manifold generates first and second recirculation flow rates;
a reagent source; and
a controller which compares each of the first and second electrical signals against predetermined signals representative of the predetermined chemical vapors and generates an alarm signal if a match exists,
wherein:
a first recirculation path operating at the first recirculation flow rate includes the first IMS, the recirculation pump, the recirculation filter, the manifold, the reagent source, and the first retainer, arranged in the stated order, one outlet of the first portion of the retainer being fluidly coupled to the input of the first IMS; and
a second recirculation path operating at the second recirculation flow rate includes the second IMS, the recirculation pump, the recirculation filter, the manifold, and second retainer, arranged in the stated order, one outlet of the second retainer being fluidly coupled to the input of the second IMS.

16. The system according to claim 15, wherein the first IMS and the second IMS each includes a radioactive source of 100 microcuries of Americium-241 ($Am^{241}$).

* * * * *